United States Patent
Giese et al.

(10) Patent No.: US 11,400,301 B2
(45) Date of Patent: Aug. 2, 2022

(54) IMPLANTABLE MEDICAL DEVICE WITH REDUCED STRESS WELDED JOINT

(71) Applicant: Cardiac Pacemakers, Inc., St. Paul, MN (US)

(72) Inventors: Troy Anthony Giese, Blaine, MN (US); Steven Lawrence Frandrup, Cottage Grove, MN (US); Emily Tubbs, St. Anthony, MN (US); Larry Michael Killeen, Elk River, MN (US); Jean M. Bobgan, Maple Grove, MN (US); David P. Stieper, North Branch, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 250 days.

(21) Appl. No.: 16/781,246

(22) Filed: Feb. 4, 2020

(65) Prior Publication Data

US 2020/0254264 A1    Aug. 13, 2020

Related U.S. Application Data

(60) Provisional application No. 62/802,991, filed on Feb. 8, 2019.

(51) Int. Cl.
*A61N 1/00* (2006.01)
*A61N 1/375* (2006.01)
(Continued)

(52) U.S. Cl.
CPC .......... *A61N 1/3756* (2013.01); *A61L 31/022* (2013.01); *B23K 26/21* (2015.10); *B23K 2101/36* (2018.08)

(58) Field of Classification Search
CPC .... A61N 1/3756; A61N 1/3758; A61N 1/378; A61N 1/375; A61L 31/022; B23K 26/21;
(Continued)

(56) References Cited

U.S. PATENT DOCUMENTS 5,712,462 A    1/1998  Berkowitz et al.
7,968,226 B2 *  6/2011  Aamodt .............. H01M 50/116
                                                 429/169

(Continued)

FOREIGN PATENT DOCUMENTS

EP      1326680      7/2003
WO      0232503      4/2002
(Continued)

OTHER PUBLICATIONS

"International Search Report and Written Opinion," for PCT Application No. PCT/US2020/016514 dated Jun. 22, 2020 (11 pages).
(Continued)

*Primary Examiner* — Scott M. Getzow
(74) *Attorney, Agent, or Firm* — Pauly, DeVries Smith & Deffner LLC

(57) ABSTRACT

Embodiments herein relate to implantable medical devices including a welded joint with reduced residual stress. In a first aspect, an implantable medical device is included having a power subunit comprising a first biocompatible electrically conductive shell, an anode disposed therein, a cathode disposed therein, and a lid. The implantable medical device can further include an electronics control subunit comprising a second biocompatible electrically conductive shell, and a control circuit disposed therein. Both of the first and second biocompatible electrically conductive shells can include first and second opposed wide sides, first and second opposed narrow sides, and four rounded corners. The first shell can be welded to the lid around a perimeter thereof forming a weld line. The weld line can have a weld line terminus and the weld line terminus can be positioned on a narrow side or a rounded corner. Other embodiments are also included herein.

19 Claims, 11 Drawing Sheets

(51) Int. Cl.
*B23K 26/21* (2014.01)
*A61L 31/02* (2006.01)
*B23K 101/36* (2006.01)

(58) Field of Classification Search
CPC ............... B23K 2101/36; B23K 26/24; A61B 2562/162; A61B 2562/187; A61B 5/076
See application file for complete search history.

(56) References Cited

U.S. PATENT DOCUMENTS

| | | | |
|---|---|---|---|
| 8,433,409 B2 | 4/2013 | Johnson et al. | |
| 9,610,451 B2 | 4/2017 | Markham et al. | |
| 2001/0049057 A1* | 12/2001 | Frustaci | H01M 50/10 429/176 |
| 2008/0045908 A1 | 2/2008 | Gould et al. | |
| 2008/0221629 A1 | 9/2008 | Morgan et al. | |
| 2014/0214128 A1* | 7/2014 | Peterson | A61N 1/3782 607/59 |
| 2016/0157371 A1 | 6/2016 | Glynn et al. | |
| 2017/0303411 A1 | 10/2017 | Bobgan et al. | |
| 2017/0317331 A1 | 11/2017 | Vedoy | |
| 2017/0332503 A1* | 11/2017 | Eppel | H05K 5/04 |
| 2018/0083256 A1 | 3/2018 | Marasco et al. | |

FOREIGN PATENT DOCUMENTS

| | | |
|---|---|---|
| WO | 2008019141 | 2/2008 |
| WO | 2020163276 | 8/2020 |

OTHER PUBLICATIONS

"International Preliminary Report on Patentability," for PCT Application No. PCT/US2020/016514 dated Aug. 19, 2021 (7 pages).

* cited by examiner

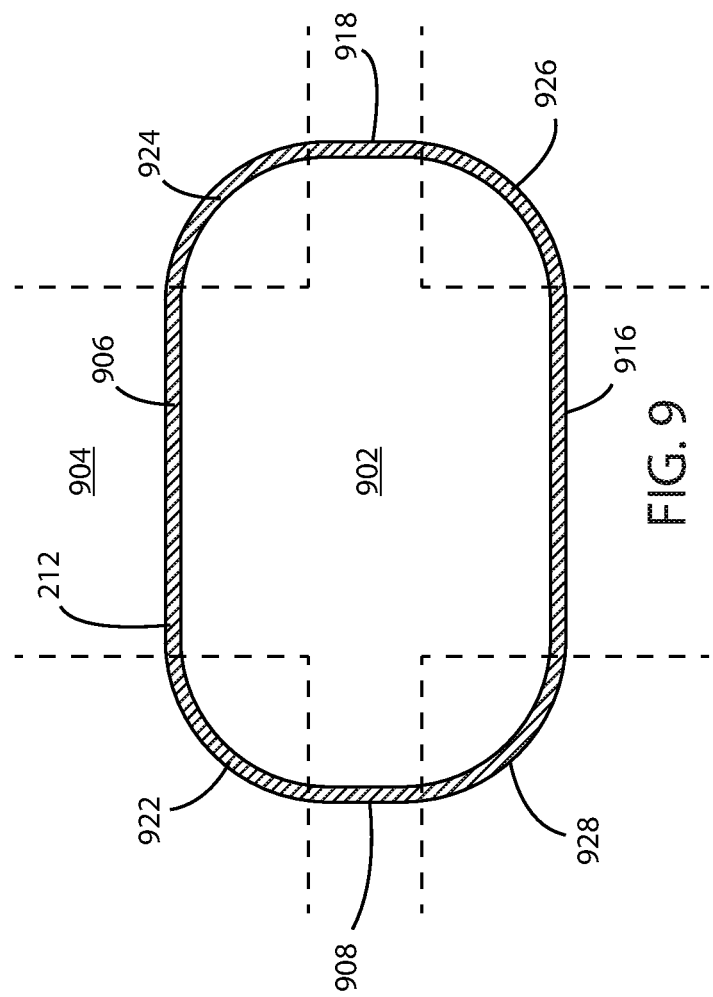

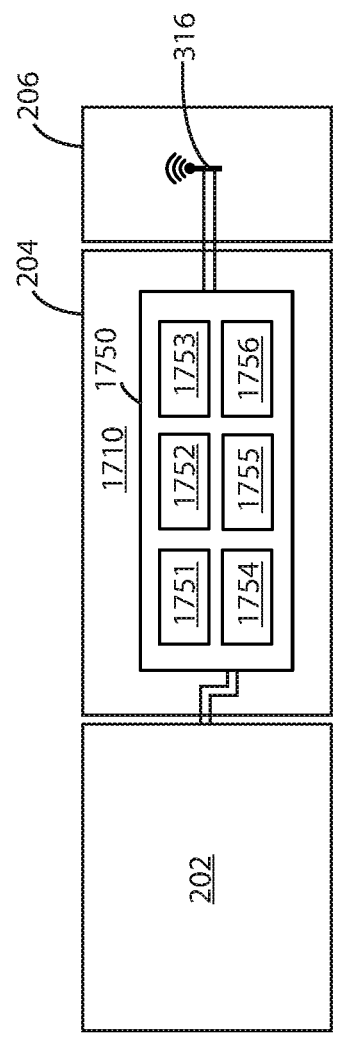

IMPLANTABLE MEDICAL DEVICE WITH REDUCED STRESS WELDED JOINT

This application claims the benefit of U.S. Provisional Application No. 62/802,991, filed Feb. 8, 2019, the content of which is herein incorporated by reference in its entirety.

FIELD

Embodiments herein relate to implantable medical devices including a welded joint with reduced residual stress.

BACKGROUND

Implantable medical devices are now commonly used for monitoring a patient's condition and in some cases also administering therapy to the patient. In some cases, the implantable medical device may be implanted only temporarily. In other cases, the implantable medical device may be implanted chronically over a period of years.

In general, it can be desirable to minimize the size of a device to be implanted in the body. Reduced size can boost patient comfort as well as allow for greater placement site and placement method flexibility. As a result, there is a general trend towards smaller and smaller devices over time. For example, state-of-the-art pacemakers are typically much smaller today than the pioneering devices of decades past. Reduced size has been made possible through advancements in the materials and component parts of devices as well as refinements of overall designs.

Metal structures can have residual stresses. Residual stresses are locked-in stresses within a metal object, even though the object is free of external forces. Residual stresses can be tensile or compressive. Residual stresses can reduce the longevity of structures they are included within.

SUMMARY

Embodiments herein relate to implantable medical devices including a welded joint with reduced residual stress. In a first aspect, an implantable medical device is included having a power subunit comprising a first biocompatible electrically conductive shell defining an open end, a closed end, and an interior volume, an anode disposed within the interior volume of the first biocompatible electrically conductive shell, a cathode disposed within the interior volume of the first biocompatible electrically conductive shell, and a lid occluding the open end of the first biocompatible electrically conductive shell. The implantable medical device can further include an electronics control subunit comprising a second biocompatible electrically conductive shell, and a control circuit disposed within the second biocompatible electrically conductive shell. The power subunit can be coupled to the electronics control subunit and the power subunit can be in electrical communication with the electronics control subunit. Both of the first and second biocompatible electrically conductive shells can include first and second opposed wide sides, first and second opposed narrow sides, wherein the narrow sides have a width less than that of the wide sides, and four rounded corners disposed at intersections between each wide side and narrow side. The first biocompatible electrically conductive shell can be welded to the lid around a perimeter of the first biocompatible electrically conductive shell forming a weld line. The weld line can have a weld line terminus, wherein the weld line terminus is positioned on a narrow side or a rounded corner.

In a second aspect, in addition to one or more of the preceding or following aspects, or in the alternative to some aspects, the weld line can include a laser weld line.

In a third aspect, in addition to one or more of the preceding or following aspects, or in the alternative to some aspects, the first biocompatible electrically conductive shell and the second biocompatible electrically conductive shell can include titanium or a titanium alloy.

In a fourth aspect, in addition to one or more of the preceding or following aspects, or in the alternative to some aspects, the weld line can be positioned on a rounded corner.

In a fifth aspect, in addition to one or more of the preceding or following aspects, or in the alternative to some aspects, wherein the weld line exhibits a residual stress that is less than an otherwise identical weld line with the weld line terminus positioned on a wide side.

In a sixth aspect, in addition to one or more of the preceding or following aspects, or in the alternative to some aspects, wherein the second biocompatible electrically conductive shell can be welded to the lid around the perimeter of the second biocompatible electrically conductive shell forming a second weld line.

In a seventh aspect, in addition to one or more of the preceding or following aspects, or in the alternative to some aspects, the second weld line having a second weld line terminus, wherein the second weld line terminus can be positioned on a narrow side or a rounded corner.

In an eighth aspect, in addition to one or more of the preceding or following aspects, or in the alternative to some aspects, the first and second biocompatible electrically conductive shells can have a thickness of 0.006 to 0.012 inches.

In a ninth aspect, in addition to one or more of the preceding or following aspects, or in the alternative to some aspects, the first and second opposed wide sides can be first and second opposed wide flat sides, and the first and second opposed narrow sides can be first and second opposed narrow flat sides.

In a tenth aspect, a method of making an implantable medical device is included. The method can include obtaining a biocompatible electrically conductive shell, the biocompatible electrically conductive shell defining an interior volume, and an open end and a closed end. The method can further include positioning a lid to occlude the open end of the biocompatible electrically conductive shell. The method can further include welding the biocompatible electrically conductive shell to the lid along a weld line, the weld line comprising a terminus. The biocompatible electrically conductive shell can include first and second opposed wide flat sides and first and second opposed narrow flat sides. The narrow flat sides can have a width less than that of the wide flat sides. Four rounded corners can be disposed between each wide flat side and an adjacent narrow flat side. The terminus of the weld line can be disposed on a narrow flat side or a rounded corner.

In an eleventh aspect, in addition to one or more of the preceding or following aspects, or in the alternative to some aspects, a method can further include welding a second biocompatible electrically conductive shell to the lid along a second weld line, the second weld line including a terminus, the second biocompatible electrically conductive shell including first and second opposed wide flat sides, first and second opposed narrow flat sides. The narrow flat sides can have a width less than that of the wide flat sides and four rounded corners can be disposed between each wide flat side and an adjacent narrow flat side. The terminus of the second weld line can be disposed on a narrow flat side or a rounded corner.

In a twelfth aspect, an implantable medical device is included having a power subunit comprising a first biocompatible electrically conductive shell, an anode disposed within the first biocompatible electrically conductive shell, a cathode disposed within the first biocompatible electrically conductive shell, and a lid. The lid can include a central body and an extended rim surrounding the central body. The first biocompatible electrically conductive shell can be welded to the extended rim of the lid.

In a thirteenth aspect, in addition to one or more of the preceding or following aspects, or in the alternative to some aspects, the extended perimeter rim can be separated from the central body by a relief channel.

In a fourteenth aspect, in addition to one or more of the preceding or following aspects, or in the alternative to some aspects, the extended perimeter rim and the first biocompatible electrically conductive shell can form a butt joint.

In a fifteenth aspect, in addition to one or more of the preceding or following aspects, or in the alternative to some aspects, the extended perimeter rim and the first biocompatible electrically conductive shell can form an overlap joint.

In a sixteenth aspect, in addition to one or more of the preceding or following aspects, or in the alternative to some aspects, the extended perimeter rim can overlap the first biocompatible electrically conductive shell.

In a seventeenth aspect, in addition to one or more of the preceding or following aspects, or in the alternative to some aspects, the lid further including a second extended rim surrounding the central body, wherein the second extended rim faces in a direction opposite that of the first extended rim.

In an eighteenth aspect, in addition to one or more of the preceding or following aspects, or in the alternative to some aspects, wherein the first biocompatible electrically conductive shell includes, in cross-section, first and second opposed wide flat sides, and first and second opposed narrow flat sides. The narrow flat sides can have a width less than that of the wide flat sides. Four rounded corners can be disposed between each wide flat side and an adjacent narrow flat side. The first biocompatible electrically conductive shell can be welded to the lid around a perimeter thereof forming a weld line. The weld line can have a weld line terminus, wherein the weld line terminus is positioned on a narrow flat side or a rounded corner.

In a nineteenth aspect, in addition to one or more of the preceding or following aspects, or in the alternative to some aspects, the weld line can be a laser weld line.

In a twentieth aspect, in addition to one or more of the preceding or following aspects, or in the alternative to some aspects, the first biocompatible electrically conductive shell can include titanium or a titanium alloy.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which:

FIG. 9 is a cross-sectional view of a shell or case as taken along line 9-9' of FIG. 4 in accordance with various embodiments herein.

FIG. 17 is a block diagram of components of an implanted medical device in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As referenced above, metal structures can have residual stresses. Residual stresses can reduce the longevity of structures they are included within. Welding operations, because of rapid thermal expansion and contraction created along a very localized area, can be a significant source of residual stress. Typically, a very high heat source is applied to a small area relative to the cooler surrounding area. The metal expands as it is brought to a molten state. As the molten weld pool solidifies along the joint, there is resistance to its shrinkage by the already solidified weld metal and the unmelted base metal adjacent to the weld. This resistance can create a tensile strain in the longitudinal and transverse directions of the weld.

Various types of implantable medical devices may include portions that are welded together, therefore creating residual stress in and around those welded portions. For example, implantable medical devices including a power subunit and an electronics control subunit may be welded together to form a unitary structure that is later implanted. The welding process creating the weld joint(s) or weld line(s) may result in significant residual stresses.

In accordance with embodiments herein, the weld joints or weld lines can be formed to minimize residual stresses. For example, it has been identified herein that the position of the end of a weld line can significantly impact the magnitude of residual stress in the area along and adjacent to the weld line. In accordance with various embodiments herein, the end of a weld line can be positioned on or around the corner of a device shell or case. In accordance with various embodiments herein, the end of a weld line can be positioned to be disposed on or around short sides of a device shell or case that is roughly rectangular in cross-section.

In accordance with embodiments herein, the structure of components that are joined with weld joints or weld lines can be manipulated to reduce minimize residual stresses. For example, the structure of a lid or interconnecting structure that is welded to a device shell or case can be formed to reduce or minimize residual stresses.

Figure 1:
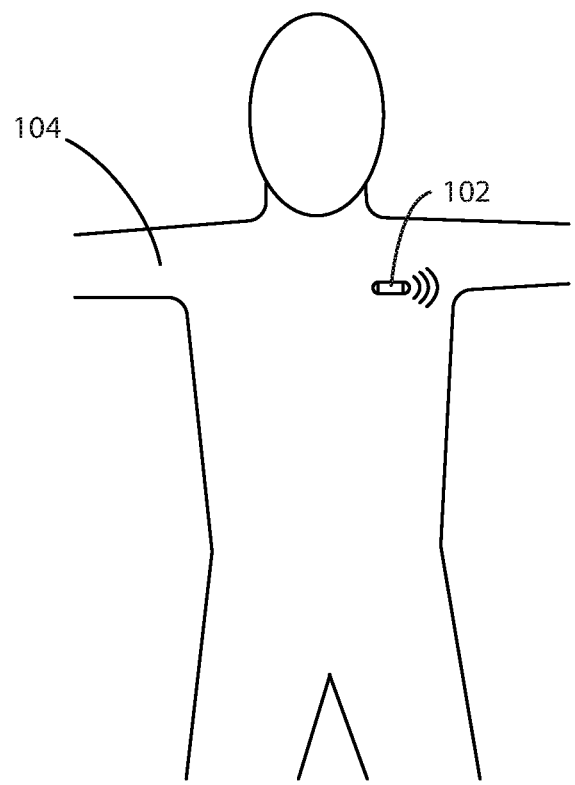
FIG. 1 is a schematic view of an implantable medical device implanted within a patient in accordance with various embodiments herein.

Referring now to FIG. 1, a schematic view is shown of an implantable medical device 102 implanted within a patient 104 in accordance with various embodiments herein. In various embodiments, at least a portion of the medical device system can be implantable. In some embodiments, the implantable medical device 102 can include an implantable loop recorder, implantable monitor device, or the like. In some embodiments, the entire implantable medical device 102 can be implanted within the body of a patient 104. Various implant sites can be used including areas on the limbs, the upper torso, the abdominal area, and the like. In some embodiments, the implantable medical device 102 can be implanted subcutaneously. In some embodiments, the medical device system can include one or more additional medical devices that are communicatively coupled to one another.

Figure 2:
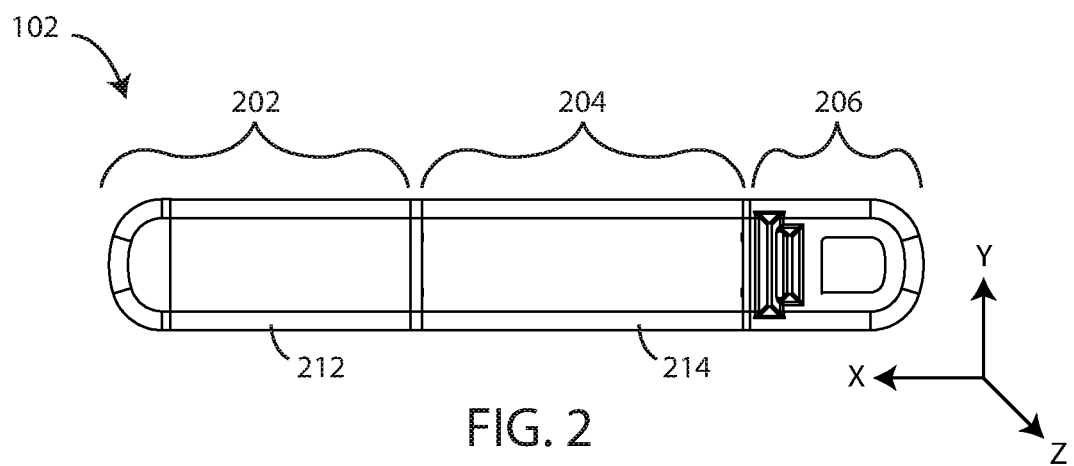
FIG. 2 is a schematic view of an implantable medical device in accordance with various embodiments herein.

Referring now to FIG. 2, a schematic view of an implantable medical device 102 is shown in accordance with various embodiments herein. The implantable medical device 102 can include a power subunit 202, an electronics control subunit 204, and a wireless communications subunit 206. The power subunit 202 can include components of an electrochemical cell. The power subunit 202 can include a first biocompatible electrically conductive shell 212 configured for direct contact with an in vivo environment. The electronics control subunit 204 can include electronic components to control operations of the device including, for example, a controller or control circuit. The electronics control subunit 204 can include a second biocompatible electrically conductive shell 214 configured for direct contact with an in vivo environment.

The power subunit 202 can be coupled to the electronics control subunit 204. In some embodiments, the power subunit 202 can be welded to the electronics control subunit 204. Welding can be performed using various techniques including laser welding. In various embodiments, the first biocompatible electrically conductive shell of the power subunit has about the same cross-sectional perimeter dimensions as the second biocompatible electrically conductive shell of the electronics control subunit. In various embodiments, the first biocompatible electrically conductive shell of the power subunit has cross-sectional perimeter dimensions that are less than 5% different than that of the second biocompatible electrically conductive shell of the electronics control subunit.

The implantable medical device 102 can have various dimensions. The overall length (X axis) can be greater than or equal to 1, 3, 5, 7, 9, 10, 12, 14, 16, 18, or 20 mm. In some embodiments, the length can be less than or equal to 80, 74, 68, 62, 56, 50, 44, 38, 32, 26, or 20 mm. In some embodiments, the length can fall within a range of 1 to 80 mm, or 3 to 74 mm, or 5 to 68 mm, or 7 to 62 mm, or 9 to 56 mm, or 10 to 50 mm, or 12 to 44 mm, or 14 to 38 mm, or 16 to 32 mm, or 18 to 26 mm, or can be about 20 mm. The overall width (Y axis) can be greater than or equal to 1.0 mm, 1.8 mm, 2.5 mm, 3.2 mm, or 4.0 mm. In some embodiments, the width can be less than or equal to 15.0 mm, 12.2 mm, 9.5 mm, 6.8 mm, or 4.0 mm. In some embodiments, the width can fall within a range of 1.0 mm to 15.0 mm, or 1.8 mm to 12.2 mm, or 2.5 mm to 9.5 mm, or 3.2 mm to 6.8 mm, or can be about 4.0 mm.

The overall depth (Z axis) can be greater than or equal to 1.0 mm, 1.8 mm, 2.5 mm, 3.2 mm, or 4.0 mm. In some embodiments, the depth can be less than or equal to 15.0 mm, 12.2 mm, 9.5 mm, 6.8 mm, or 4.0 mm. In some embodiments, the depth can fall within a range of 1.0 mm to 15.0 mm, or 1.8 mm to 12.2 mm, or 2.5 mm to 9.5 mm, or 3.2 mm to 6.8 mm, or can be about 4.0 mm.

Figure 3:
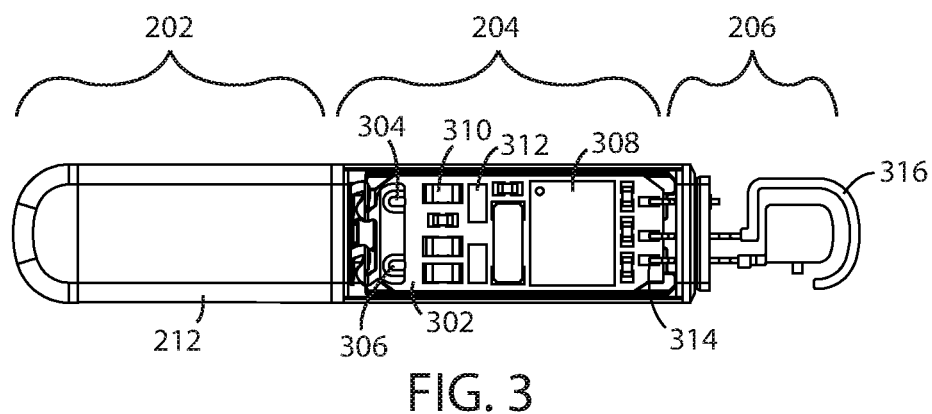
FIG. 3 is a schematic view of an implantable medical device in accordance with various embodiments herein.

Referring now to FIG. 3, a schematic view of an implantable medical device 102 is shown in accordance with various embodiments herein. In this view, the electrically conductive shell 214 has been removed to show the components within the electronics control subunit 204 of the implantable medical device. The electronics control subunit 204 can include a circuit board 302 and power input connections 304, 306 which can be in electrical communication with output pins of the power subunit 202. The electronics control subunit 204 can further include a controller 308 which can form part of a control circuit. The electronics control subunit 204 can further circuit components 310 and 312. It will be appreciated that many different circuit components can be included such as integrated circuits of various types, signal processing chips, ASICs (application specific integrated circuits), clock circuits, capacitors, and the like. The electronics control subunit 204 can also include I/O pins 314. The total number of I/O pins (digital or analog) is not particularly limited. The wireless communications subunit 206 can include an antenna 316, which can be in electrical communication with I/O pins 314. In some embodiments, one of the I/O pins 314 can be a negative bias output pin, which can be regulated to provide a relative negative electrical potential.

Figure 4:
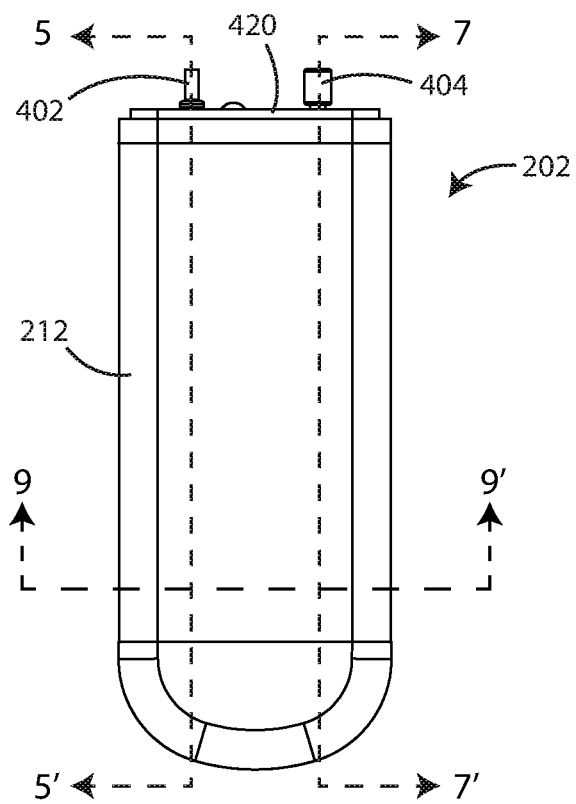
FIG. 4 is a power subunit in accordance with various embodiments herein.

Referring now to FIG. 4, a power subunit 202 is shown in accordance with various embodiments herein. The power subunit 202 can include electrically conductive shell 212. The electrically conductive shell can include a closed end and an open end and can define an interior volume therein. The power subunit 202 can further include a lid 420, which can be attached (such as by welding or another technique) to the electrically conductive shell 212 and can occlude the open end of the electrically conductive shell. The power subunit 202 can further include an anode pin 402 and a cathode pin 404. Anode pin 402 and cathode pin 404 can be formed of various conductive materials such as metals. In some embodiments, the anode pin 402 and/or the cathode pin 404 are formed of molybdenum or a molybdenum containing alloy. However, many different pin materials are contemplated herein.

In various embodiments, the implantable medical device can be configured so that the biocompatible electrically conductive shell 212 of the power subunit 202 and/or electrically conductive shell of the electronics control subunit 204 has a relative positive, negative, or neutral electrical potential.

Figure 6:
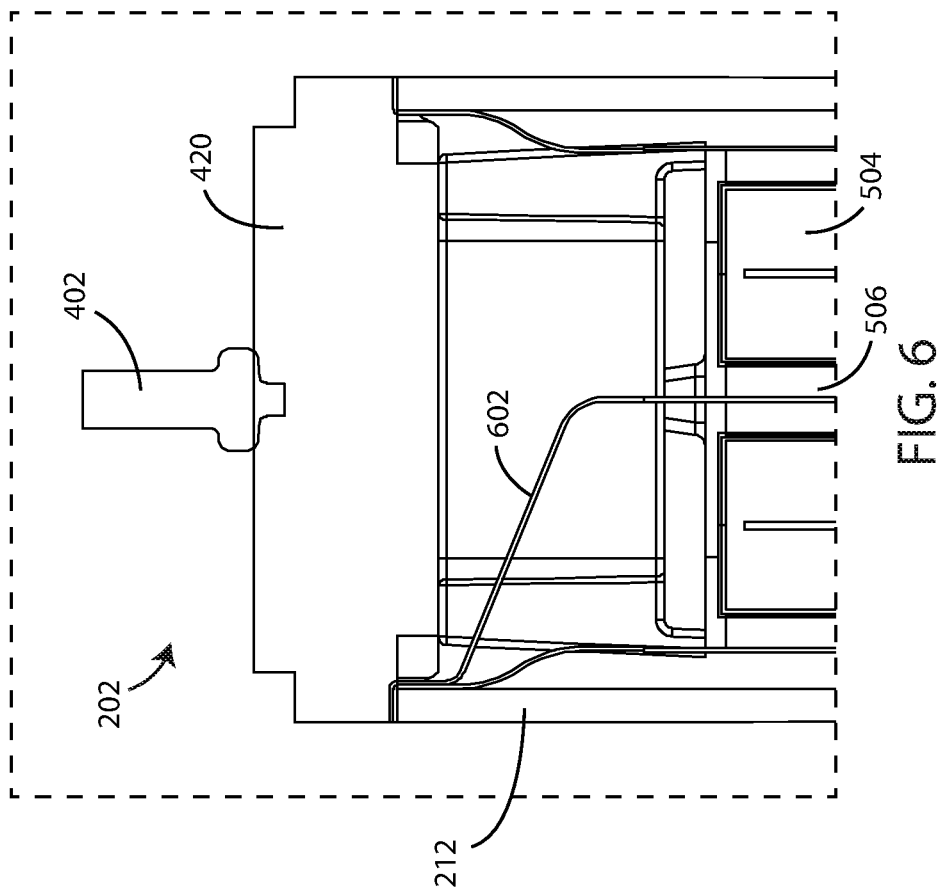
FIG. 6 is an enlarged view of a portion of FIG. 5 in accordance with various embodiments herein.
Figure 5:
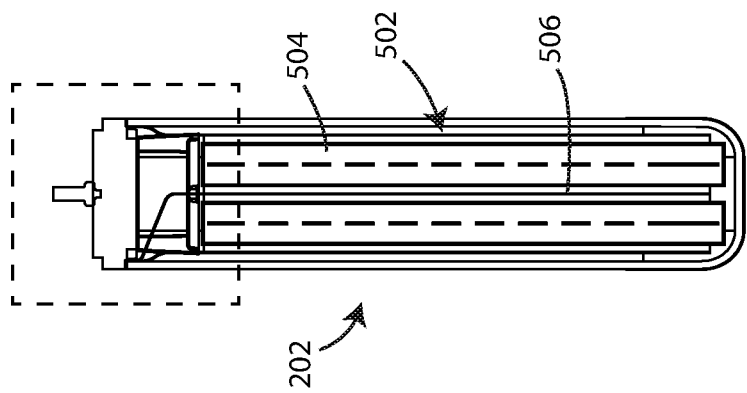
FIG. 5 is a cross-sectional view of a power subunit as taken along line 5-5' of FIG. 4 in accordance with various embodiments herein.

Referring now to FIG. 5, a cross-sectional view of the power subunit 202 is shown as taken along line 5-5' of FIG. 4 in accordance with various embodiments herein. The power subunit 202 can include components of an electrochemical cell 502 including a cathode 504 and an anode 506. Referring now to FIG. 6, an enlarged view of a portion of FIG. 5 is shown in accordance with various embodiments herein. In this view, it can be seen that the power subunit 202 can include an anode pin 402 and a lid 420. Further, an anode connection tab 602 can provide electrical communication between the anode 506 and the lid 420 and the shell 212 or case of the power subunit 202, thus provide the shell 212 or case with a relative negative electrical potential.

Figure 8:
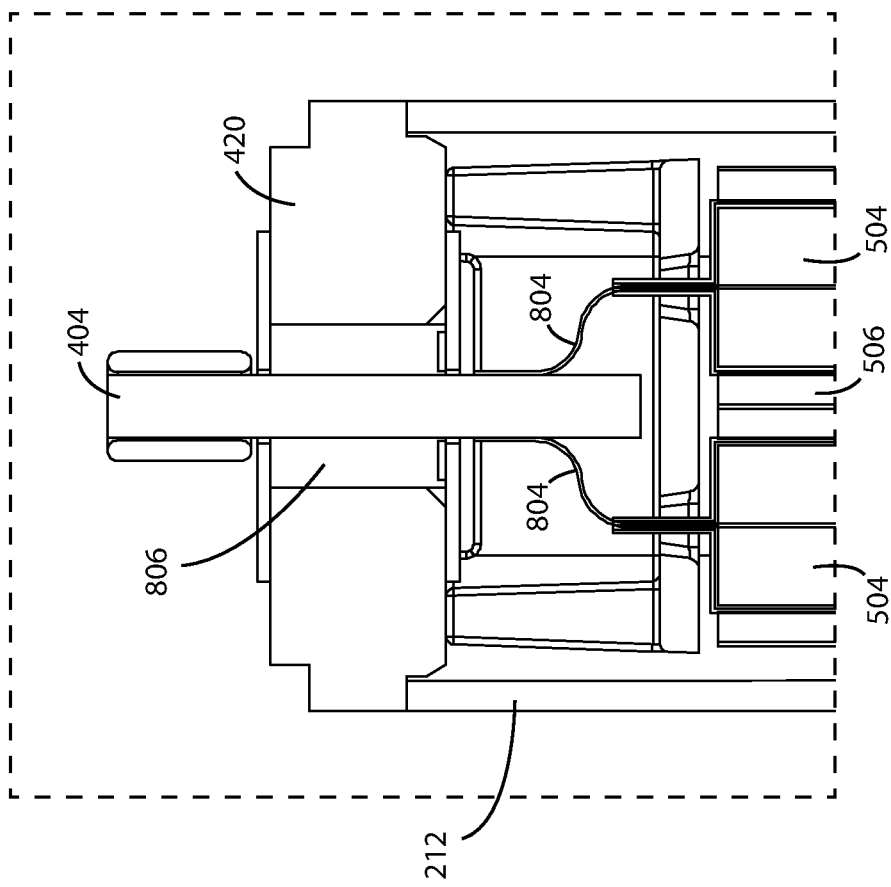
FIG. 8 is an enlarged view of a portion of FIG. 7 in accordance with various embodiments herein.
Figure 7:
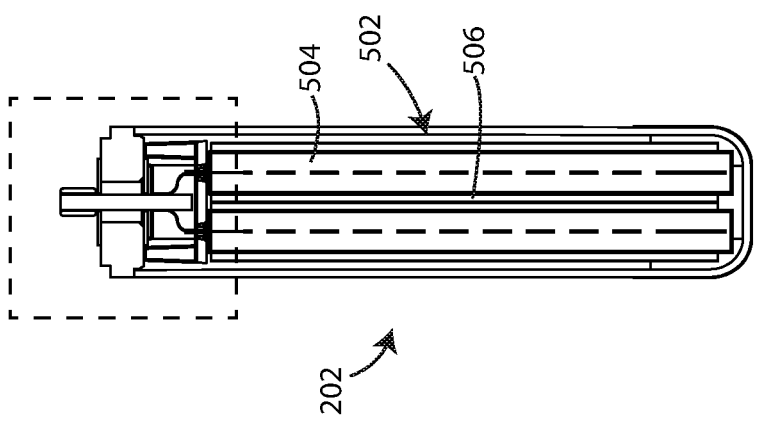
FIG. 7 is a cross-sectional view of a power subunit as taken along line 7-7' of FIG. 4 in accordance with various embodiments herein.

Referring now to FIG. 7, a cross-sectional view of the power subunit 202 is shown as taken along line 7-7' of FIG. 4 in accordance with various embodiments herein. Again, the power subunit 202 can include components of an electrochemical cell 502 including a cathode 504 and an anode 506. Referring now to FIG. 8, an enlarged view of a portion of FIG. 7 is shown in accordance with various embodiments herein. In this view, it can be seen that the power subunit 202 can include a cathode pin 404 and a lid 420. Further, cathode connection tabs 804 can provide electrical communication between the cathode 504 and the cathode pin 404. A feedthrough structure 806 can serve to electrically isolate the cathode pin 404 from the shell 212 and case of the power subunit 202. The feedthrough structure 806 can be formed of a non-conductive material such as a non-conductive ceramic, glass, polymer, composite, or the like.

It will be appreciated that while the embodiment shown in FIGS. 4-8 provides for a relatively negative electrical potential for the biocompatible electrically conductive shell 212 of the power subunit 202, that other configurations are contemplated herein. In specific, configurations with neutral or relatively positive electrical potentials are contemplated herein.

It has been found that residual stress can be reduced by careful placement of the end of a weld line. For example, it has been found that residual stress can be reduced by placing the end (or terminus) of a weld line in a corner or along a narrow side (such as a narrow flat side) of the shell or housing. Thus, when the weld line terminus is placed in a corner or along a narrow side, the weld line exhibits a residual stress that is less than an otherwise identical weld line with a weld line terminus positioned on a wide side (or wide flat side).

Referring now to FIG. 9, a cross-sectional view of a shell 212 or case as taken along line 9-9' of FIG. 4 is shown in accordance with various embodiments herein. The shell 212 defines an interior volume 902 including which various components can be placed, such as in the context of a power subunit components of an electrochemical cell. The outside 904 of the shell 212 can be an in vivo environment after the device is implanted within a subject.

The shell can include first and second opposed wide sides 906, 916 (such as wide flat sides), first and second opposed narrow sides, 908, 918 (such as narrow flat sides), wherein the narrow sides have a width less than that of the wide sides. The wide sides can have a width that is 5, 10, 25, 50, 75, 100, 150, 200, or 300 percent or more (or an amount falling within a range between any of the foregoing) greater than that of the narrow sides. The shell 212 can also include four rounded corners 922, 924, 926, and 928 disposed between each wide side and adjacent narrow side. The four rounded corners can be disposed at intersections between each wide side and narrow side. In some embodiments, the wide sides can be substantially flat. However, in other embodiments, the wide sides can include a degree of curvature. In some embodiments, the narrow sides can be substantially flat. However, in other embodiments, the narrow sides can include a degree of curvature.

In some embodiments, the thickness of the shell 212 can be greater than or equal to 0.004 inches, 0.005 inches, 0.006 inches, 0.007 inches, or 0.008 inches. In some embodiments, the thickness of the shell 212 can be less than or equal to 0.016 inches, 0.014 inches, 0.012 inches, 0.011 inches, 0.010 inches, 0.009 inches, or 0.008 inches. In some embodiments, the thickness of the shell 212 can fall within a range of 0.004 inches to 0.014 inches, 0.004 inches to 0.012 inches, or 0.005 inches to 0.011 inches, or 0.006 inches to 0.010 inches, or 0.007 inches to 0.009 inches, or can be about 0.008 inches on average (mean).

In some embodiments, the shell 212 can be deep drawn. However, deep drawing can result in a structure with higher residual stress and a greater number of surface cracks which can serve as concentration points for stress. In some embodiments, the shell 212 can be machined (e.g., can have machined surfaces). Machining the structure can result in reduced residual stress and fewer surface cracks. In some embodiment, the surface roughness (inside surface and/or outside surface) can be less than or equal to 40, 30, 25, 20, 15, 10, or 8 μin Ra, or can be an amount falling within a range between any of the foregoing. Other techniques for forming the shell 212 can include stamping processes, additive manufacturing processes, and the like.

The shell 212 can be formed of various materials. In some embodiments, the shell 212 can include a metal. In some embodiments, the shell 212 can include one or more of titanium, titanium alloys, stainless steel, cobalt-chromium alloys, and the like.

Figure 10:
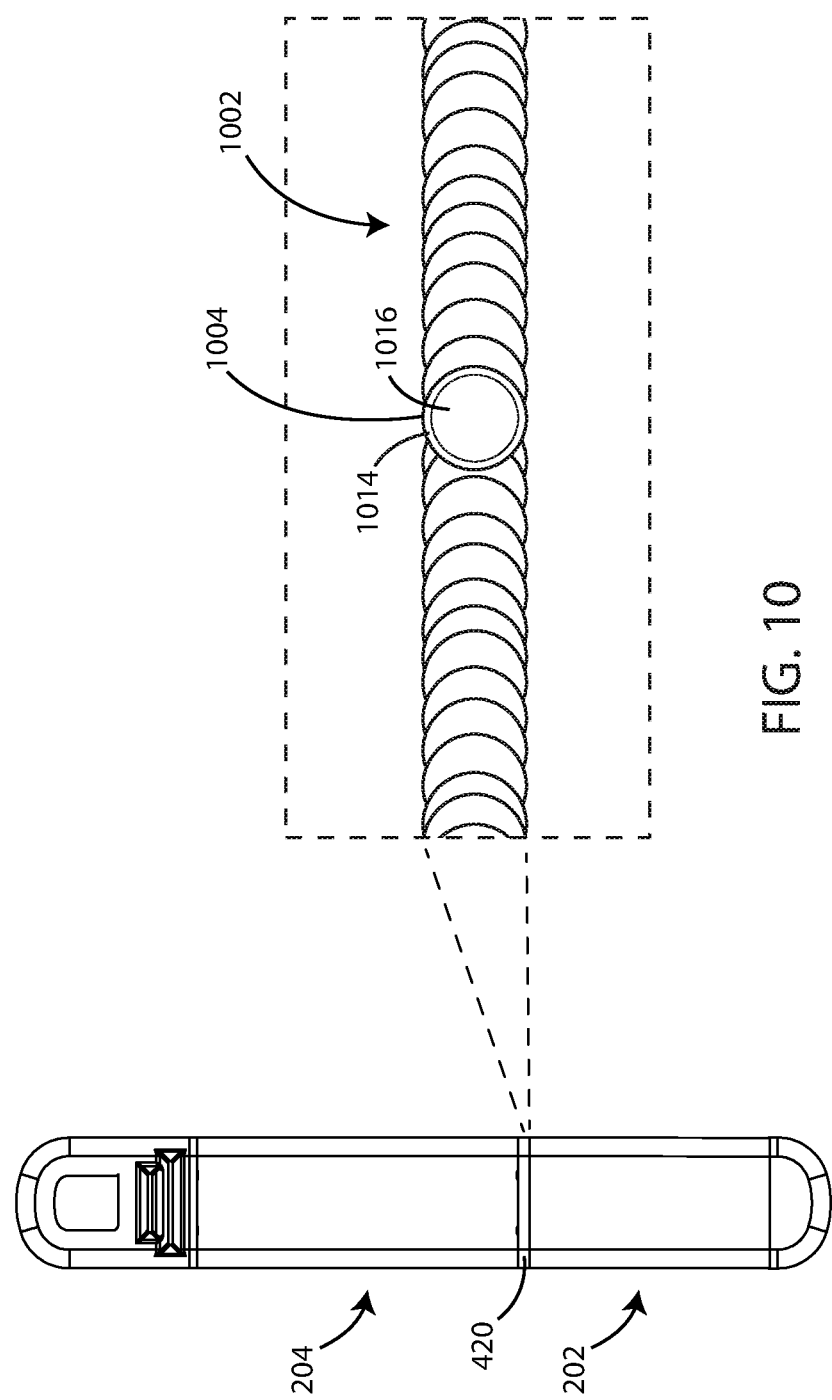
FIG. 10 is a schematic view showing a weld line on an implantable medical device in accordance with various embodiments herein.

Referring now to FIG. 10, a schematic view is shown of a weld line on an implantable medical device in accordance with various embodiments herein. The implantable medical device can include a power subunit 202 and an electronics control subunit 204. A lid 420 or interconnecting structure is shown between the power subunit 202 and an electronics control subunit 204. An exemplary weld line 1002 or joint can include a weld line terminus 1004 or end. The weld line 1002 shown can represent a weld line between the shell or case of the power subunit 202 and the lid 420, or a weld line between the shell or case of the electronics control subunit 204 and the lid 420, or a weld line directly between the shell or case of the power subunit 202 and the shell or case of the electronics control subunit 204, or more than one of these (it being appreciated that the implantable medical device can include more than one weld line).

The weld line terminus 1004 or terminus can be characterized by a circular perimeter, typically forming an unbroken circle, that results in the last area where the energy is applied to cause welding (such as the last place where laser energy is applied). In some cases, there is a slight depression 1016 in the center of the weld line terminus 1004 relative to a slightly raised ring 1014 forming the perimeter of the weld line terminus 1004. In some embodiments, the difference in height between the depression 1016 and the surrounding ring 1014 can be greater than or equal to 0.0000, 0.0001, 0.0002, 0.0003, 0.0004, or 0.0005 thousandths of an inch. In some embodiments, the difference in height can be less than or equal to 0.0020, 0.0017, 0.0014, 0.0011, 0.0008, or 0.0005 thousandths of an inch. In some embodiments, the difference in height can fall within a range of 0.0000 to 0.0020 thousandths, or 0.0001 to 0.0017 thousandths, or 0.0002 to 0.0014 thousandths, or 0.0003 to 0.0011 thousandths, or 0.0004 to 0.0008 thousandths of an inch. Aspects of welding are described in greater detail below.

Figure 11:
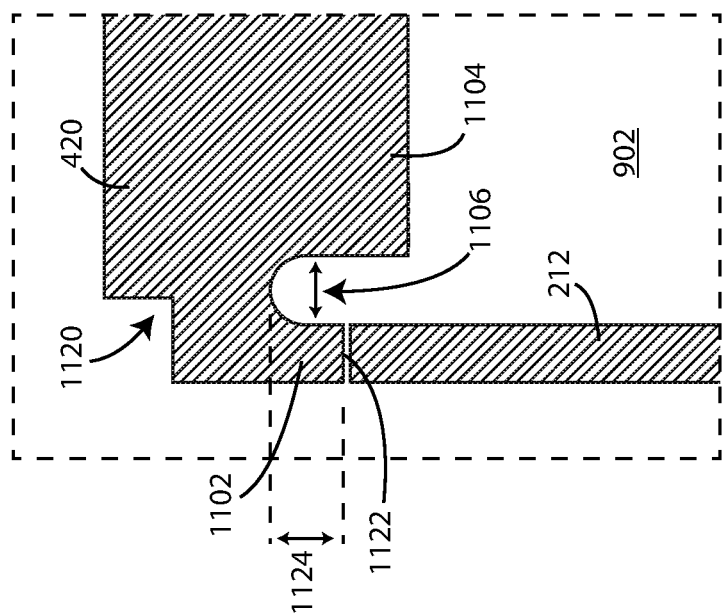
FIG. 11 is a partial cross-sectional view of a joint between a shell or case and a lid in accordance with various embodiments herein.

In accordance with embodiments herein, the structure of components that are joined with weld joints or weld lines can be manipulated to reduce minimize residual stresses. For example, the structure of a lid or interconnecting structure that is welded to a device shell or case can be formed to reduce or minimize residual stresses. Referring now to FIG. 11, a partial cross-sectional view is shown of a joint between a shell 212 or case and a lid 420 in accordance with various embodiments herein. The lid 420 comprises a central body 1104 and an extended rim 1102 surrounding the central body 1104. The extended rim 1102 can be a perimeter rim. The shell 212 or case can be welded to the extended rim 1102 of the lid 420. The extended rim 1102 can be separated from the central body 1104 by a relief channel 1106. The relief channel 1106 can provide a mechanical separation between the end 1122 of the extended rim 1102 and the central body 1104. The lid 420 can also include a ledge 1120 or bevel to interface with and form a joint with another shell or case, such as the shell or case of an electronics control subunit 204.

In some embodiments, the relief channel 1106 can have a width of about 0.1, 0.25, 0.5, 0.75, 1, 1.5, 2, 2.5, 3, 3.5, or 4 mm, or an amount falling within a range between any of the foregoing. The length 1124 of the extended rim 1102 with respect to the depth of the relief channel 1106 can be about 0.1, 0.15, 0.2, 0.25, 0.5, 0.75, 1, 1.5, 2, 2.5, 3, 4, 5, 6 mm or more, or can be an amount falling within a range between any of the foregoing. The thickness of the extended rim 1102 can be roughly equivalent to the thickness of the shell 212. However, in some embodiments the extended rim 1102 can be thicker or thinner than the shell 212.

Figure 12:
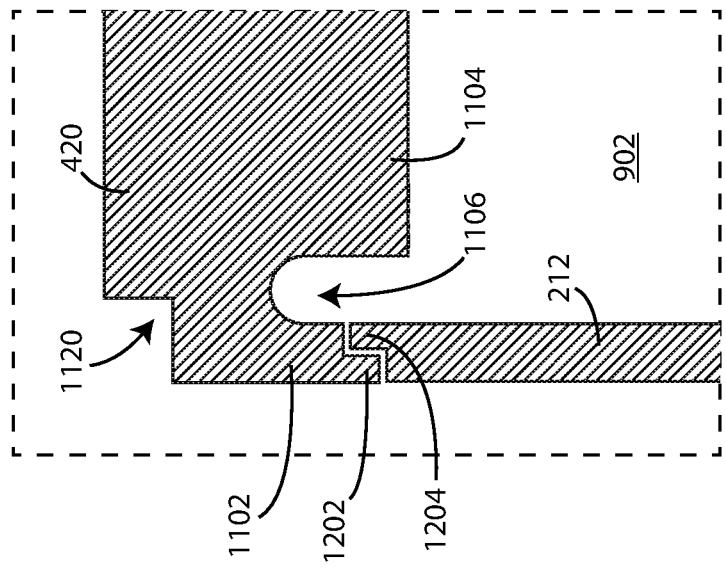
FIG. 12 is a partial cross-sectional view of a joint between a shell or case and a lid in accordance with various embodiments herein.

Many different variations for the joint between the shell or case and the lid are contemplated herein. Referring now to FIG. 12, a partial cross-sectional view is shown of a joint between a shell 212 or case and a lid 420 in accordance with various embodiments herein. The embodiment of FIG. 12 is similar to that of FIG. 11. However, in this embodiment, the interface between the shell 212 and the extended rim 1102 is formed by opposed tongues 1202, 1204 creating a lap joint.

Figure 13:
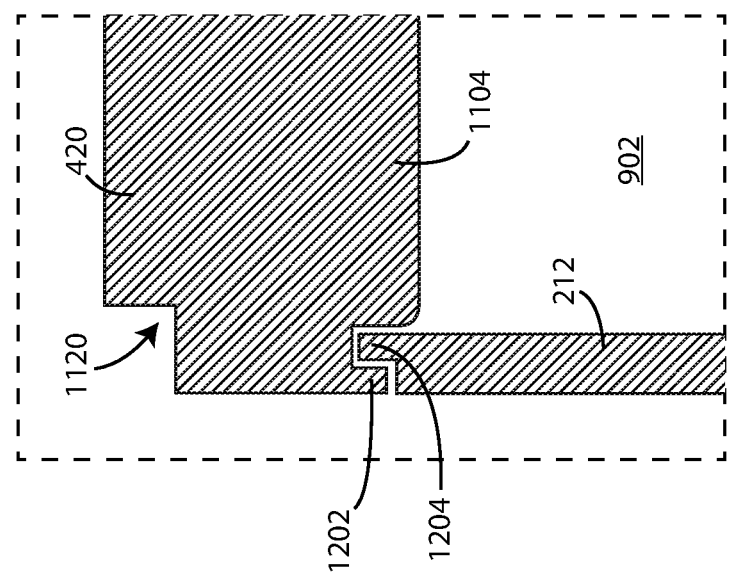
FIG. 13 is a partial cross-sectional view of a joint between a shell or case and a lid in accordance with various embodiments herein.

However, it will be appreciated that in some embodiments, a relief channel 1106 can be substantially reduced in size or even omitted. Referring now to FIG. 13, a partial cross-sectional view is shown of a joint between a shell 212 or case and a lid 420 in accordance with various embodiments herein. In this embodiment, the interface between the shell 212 and the lid 420 is formed by opposed tongues 1202, 1204 creating a lap joint.

Figure 14:
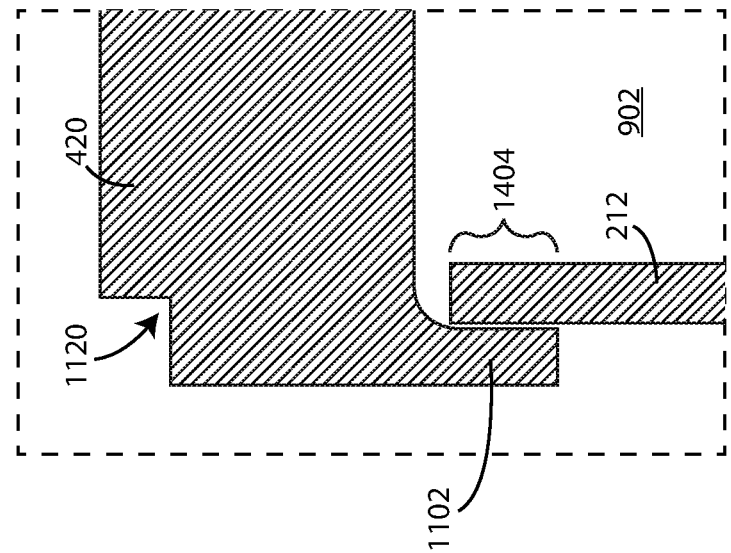
FIG. 14 is a partial cross-sectional view of a joint between a shell or case and a lid in accordance with various embodiments herein.

In some embodiments, an extended perimeter rim may be formed even in the absence of a relief channel. Further, in some embodiments, an extended perimeter rim can overlap the shell or case (to the inside or to the outside). Referring now to FIG. 14, a partial cross-sectional view is shown of a joint between a shell 212 or case and a lid 420 in accordance with various embodiments herein. In this embodiment, there is a neck region 1404 between the extended rim 1102 and the shell 212. The neck region 1404 can vary in size. In some embodiments the overlapping region can be about 0.5, 0.75, 1, 1.5, 2, 3, 4, 5 mm or more, or can be an amount falling within a range between any of the foregoing. In some embodiments the overlapping region can be a full-thickness overlap between the extended rim 1102 and the shell 212. In other embodiments, the overlapping region can be a partial-thickness overlap.

In the context of an embodiment with an overlapping region between the extended rim 1102 and the shell 212, in some cases the shell 212 can fit within the rim 1102 and therefore have a smaller outside perimeter than the rim 1102. In other cases, the shell 212 can fit over the rim 1102 and therefore have a larger outside perimeter than the rim 1102. In still other cases, the shell 212 can be necked inward at the top thereof such that a portion of the shell 212 can fit within the outside perimeter of the rim 1102, but the remainder of the shell 212 can have an outside perimeter that is similar to or the same as the lid 420 and/or a rim 1102 thereof.

Figure 15:
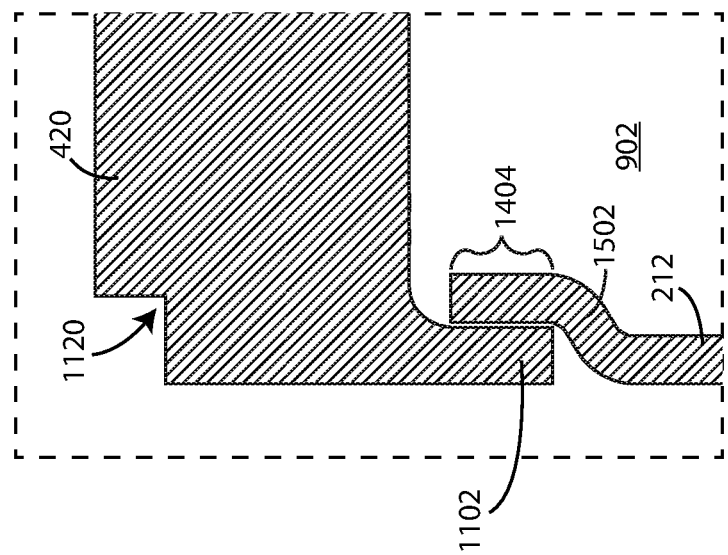
FIG. 15 is a partial cross-sectional view of a joint between a shell or case and a lid in accordance with various embodiments herein.

Referring now to FIG. 15, a partial cross-sectional view is shown of a joint between a shell 212 or case and a lid 420 in accordance with various embodiments herein. In this embodiment, a neck region 1404 can be formed at the top of the shell 212 through an inward curvature 1502 of the shell 212 in an area near where the shell 212 interfaces with a lid 420 and/or a rim 1102 thereof. In some embodiments, the neck region 1404 can be necked inward by a distance approximately equivalent to the thickness of the shell 212 and/or the thickness of a rim 1102.

In some embodiments, a lid can be constructed such that a relief channel is formed only on one side. For example, a lid can be constructed so that only the interface with a shell of one component (e.g., power subunit or electronics control subunit) can be separated from the main body of the lid by a relief channel. In this regard, the lid can have an asymmetrical construction from top to bottom (with respect to the orientation shown in FIGS. 11-16). However, in other embodiments, a relief channel can be formed on both sides such that both the interface between a shell of power subunit and the shell of an electronics control subunit can both be separated from the main body of the lid by relief channels.

Figure 16:
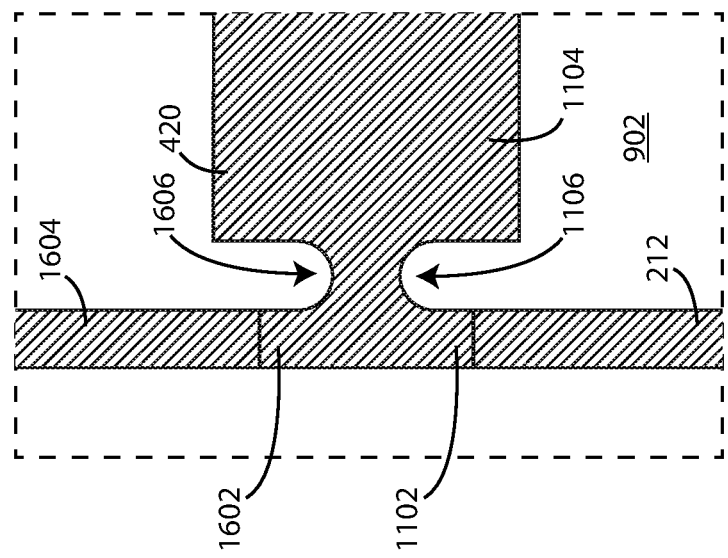
FIG. 16 is a partial cross-sectional view of a joint between a shell or case and a lid in accordance with various embodiments herein.

Referring now to FIG. 16, a partial cross-sectional view is shown of a joint between a shell 212 or case and a lid 420 in accordance with various embodiments herein. In this embodiment, the lid 420 comprises a central body 1104 and a first extended rim 1102 surrounding the central body 1104. The lid 420 also include a second extended rim 1602 surrounding the central body 1104 that is facing in a direction opposite of the first extended rim 1102. The first shell 212 or case can be welded to the first extended rim 1102 and a second shell 1212 or case can be welded to the second extended rim 1602. The first extended rim 1102 can be separated from the central body 1104 by a first relief channel 1106 and the second extended rim 1602 can be separated from the central body 1104 by a second relief channel 1606. The first relief channel 1106 can provide a mechanical separation between the end of the first extended rim 1102 and the central body 1104. The second relief channel 1606 can provide a mechanical separation between the end of the second extended rim 1602 and the central body 1104. In some embodiments, the first relief channel 1106 and the second relief channel 1606 can be substantially identical in terms of size and shape, but in other embodiments they can be different. Similarly, in some embodiments the first extended rim 1102 and the second extended rim 1602 can be substantially identical in terms of size and shape, but in other embodiments they can be different.

System Components

It will be appreciated that the implantable medical device can include many different components depending on the desired functionality. Referring now to FIG. 17 a block diagram is shown of components of an implanted medical device in accordance with various embodiments herein. However, it will be appreciated that various specific embodiments can include a greater number of components, a lesser number of components, or different components. In this example, the implantable medical device 102 can include circuitry 1750. The circuitry 1750 can include various electrical components, including, but not limited to a controller 1751 (which can form part of a control circuit), a sensor 1752 (e.g., an accelerometer, a gyroscope, a microphone, a bio-impedance sensor), a microprocessor 1753, therapy unit circuitry 1754, recorder circuitry 1755, and sensor interface circuitry 1756. Other examples of components suitable for use in the medical device systems embodied herein can include telemetry circuitry, memory circuitry (e.g., such as random access memory (RAM) and/or read only memory (ROM)), power supply circuitry (which can include, but not be limited to, one or more batteries, a capacitor, a power interface circuit, etc.), normalization circuitry, control circuitry, electrical field sensor and stimulation circuitry, display circuitry, and the like.

In some embodiments, one or more components can be integrated into the implantable medical device and in other embodiments one or more components can be separate. In some embodiments recorder circuitry can record the data produced by the sensors of the device and record time stamps regarding the same. In some embodiments, the circuitry can be hardwired to execute various functions while in other embodiments, the circuitry can be implemented as instructions executing on a controller, a microprocessor, other computation device, application specific integrated circuit (ASIC), or the like.

In some embodiments, the implantable medical device 102 can include a chemical sensor. In some embodiments, the chemical sensor is an optical chemical sensor. However, in other embodiments the chemical sensor can be a potentiometric chemical sensor. The chemical sensor can specifically include at least one chemical sensing element, an optical window, and an electro-optical module. The electro-optical module can be in electrical communication with the circuitry within the interior volume 1710. In some embodiments, the chemical sensor can be configured to measure a cellular interstitial component, a blood component, or a breath component, or any analytes thereof. In some embodiments the blood component can include blood constituents or analytes thereof, such as red blood cells; white blood cells including at least neutrophils, eosinophils, and basophils; platelets; hemoglobin; and the like.

The implantable medical device 102 can include a controller 1751. In some embodiments, the controller 1751 can be configured to execute one or more operations described herein. The implantable medical device 102 can include additional components, for example, a therapy unit circuitry 1754. The therapy unit circuitry 1754 can be configured to deliver a therapy to a patient and/or control or influence the delivery of a therapy provided by another device. In some embodiments, the therapy unit can be configured to provide optimum therapy to a patient depending on if they are in a recumbent, standing or sitting position. Examples of therapies can include, but are not limited to, pacing schemes such as rate-adaptive pacing, cardiac-resynchronization therapy (CRT), delivery of a neurostimulation therapy, administration of therapeutic agents, and the like. In some embodiments, the therapy unit circuitry 1754 can be a pharmaceutical therapy unit. In some embodiments, the therapy unit circuitry 1754 can include both an electrical therapy unit and a pharmaceutical therapy unit. In some embodiments, the therapy unit circuitry 1754 can be directed by the controller 1751 to deliver a therapy to a patient.

Figure 18:
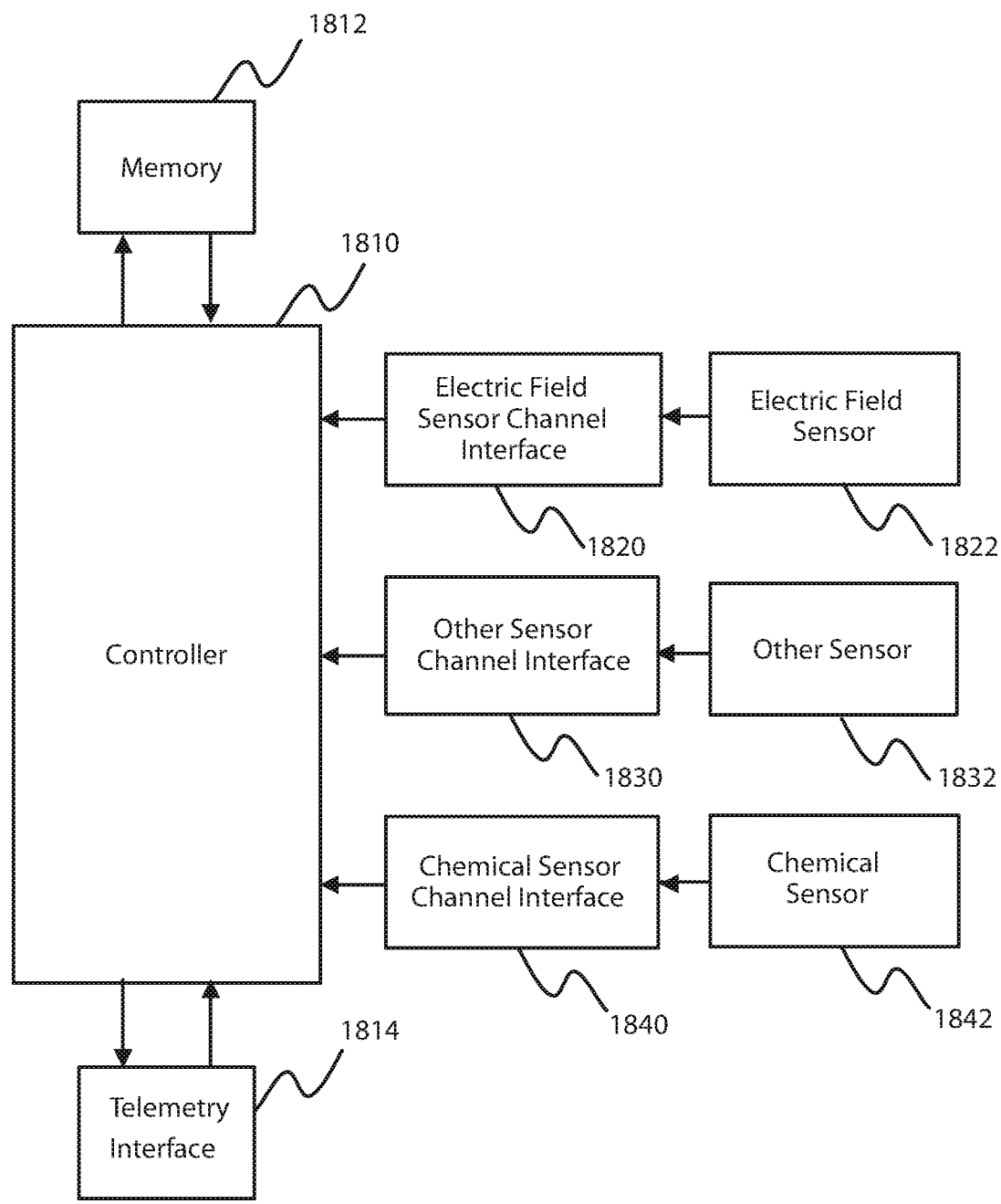
FIG. 18 is a schematic diagram of components of an implantable medical device in accordance with various embodiments herein.

Referring now to FIG. 18 is a schematic diagram of components of an implantable medical device in accordance with various embodiments herein. Elements of some embodiments of a medical device system are shown in FIG. 18 in accordance with the embodiments herein. However, it will be appreciated that some embodiments can include additional elements beyond those shown in FIG. 18. In addition, some embodiments may lack some elements shown in FIG. 18. The medical device, as embodied herein, can gather information through one or more sensing channels 1820, 1830, 1840. A controller 1810 can communicate with a memory 1812 via a bidirectional data bus. The memory 1812 can include read only memory (ROM) or random access memory (RAM) for program storage and RAM for data storage.

In some embodiments, a medical device can include one or more electric field sensors 1822 (i.e., electrodes) and an electric field sensor channel interface 1820 that can communicate with a port of controller 1810. The medical device can also include another type of sensor 1832 and a sensor channel interface 1830 for the same that can communicate with a port of controller 1810. The medical device can also include one or more chemical sensors 1842 and a chemical sensor channel interface 1840 that can communicate with a port of controller 1810. The channel interfaces 1820, 1830 and 1840 can include various components such as analog-to-digital converters for digitizing signal inputs, sensing amplifiers, registers that can be written to by the control circuitry to adjust the gain and threshold values for the sensing amplifiers, and the like. A telemetry interface 1814 is also provided for communicating with external devices such as a programmer, a home-based unit, and/or a mobile unit (e.g. a cellular phone, laptop computer, etc.).

In some embodiments, the medical device can also include additional sensors, such as posture sensors, activity sensors, or respiration sensors integral to the medical device. In some embodiments, the medical device can also include additional sensors that are separate from medical device. In various embodiments one or more of the posture sensors, activity sensors, or respiration sensors can be within another implanted medical device communicatively coupled to the medical device via telemetry interface 1814. In various embodiments one or more of the additional posture sensors, activity sensors, or respiration sensors can be external to the body and are coupled to medical device via telemetry interface 1814.

Welding

Various welding techniques can be used. However, in many embodiments, the weld line can be formed using a laser welding technique (or laser beam welding). The laser system can be a solid-state laser system or a gas laser system. Exemplary laser systems can include, but are not limited to, ruby lasers and Nd:YAG lasers, though other laser systems are also contemplated herein. The spot size of the laser can vary. In some embodiments, the spot size can be about 0.05, 0.1, 0.2, 0.3, 0.4, or 0.5 mm, or can fall within a range between any of the foregoing. The power density can be about 0.1, 0.25, 0.5, 0.75, 1.0, 1.5, 2, 4, 6, or 8 MW/cm$^2$, or an amount falling within a range between any of the foregoing. The depth of penetration can be proportional to the amount of power supplied, but also dependent on the location of the focal point. Continuous or pulsed laser beam approaches can be used. In various embodiments herein, a pulsed laser beam approach can be used. In various embodiments, the pulses can be from one to several milliseconds. In various embodiments herein, the weld line is not full thickness with respect to the materials being welded together, such as in scenarios where the weld is being applied to a butt joint. However, in other embodiments, the weld could be full thickness. In various embodiments, the weld line can penetrate 5, 10, 20, 30, 40, 50, 60, 70, 80, 90, or 100 percent of the thickness of the materials being welded together, or an amount falling within a range between any of the foregoing.

Battery Chemistries

In various embodiments herein, the electrochemical cell can be a primary lithium-manganese dioxide (Li anode/MnO$_2$ cathode) battery. However, other primary lithium battery chemistries are also contemplated herein. Other primary battery chemistries can include, but are not limited to, CFx, SVO, hybrid CFx/Mn02, hybrid CFx/SVO, and the like.

In various embodiments, the lithium battery can be constructed from a number of thin sheets of different materials that are sandwiched together to form a battery assembly. A repeating arrangement within the cell can include an anode assembly, a separator, and a cathode. The anode assembly can be formed from a sheet of lithium material that constitutes an anode and a material that constitutes a current collector. A sheet of lithium material can be laminated to a substrate, such as a current collector. The current collector can be constructed from a number of different materials. For example, the current collector can be constructed from, among other alternatives, nickel or nickel-based material, stainless steel, aluminum, titanium, or copper, or any other suitable material. The current collector can include a uniform sheet, a wire grid, or other configurations. Further details of exemplary electrochemical cell components are described in U.S. Publ. Pat. Appl. Nos. 2008/0221629 and 2017/0317331, the content of which is herein incorporated by reference.

Various electrolyte compositions can be used with electrochemical cells or batteries herein. In some embodiments, the electrolyte can be non-aqueous (e.g., organic only electrolyte solvent). In some embodiments, the electrolyte is a 1M LiTFSi solution in ethylene carbonate, propylene carbonate and dimethoxy ethane. Various separators can be used with electrochemical cells or batteries herein.

Methods

Embodiments herein also include various methods. By way of example, embodiments of making implantable medical devices as described herein are included. Further, embodiments of using implantable medical devices as described herein are included.

In an embodiment, a method of making an implantable medical device is included. The method can include obtaining a biocompatible electrically conductive shell, the biocompatible electrically conductive shell defining an interior volume, an open end and a closed end. The method can further include positioning a lid to occlude the open end of the biocompatible electrically conductive shell. The method can further include welding the biocompatible electrically conductive shell to the lid along a weld line, the weld line comprising a terminus. The biocompatible electrically conductive shell can include first and second opposed wide sides (or wide flat sides) and first and second opposed narrow sides (or narrow flat sides). The narrow flat sides can have a width less than that of the wide flat sides. Four rounded corners can be disposed between each wide flat side and an adjacent narrow flat side. The terminus of the weld line can be disposed on a narrow flat side or a rounded corner.

In various embodiments, the method can further include welding a second biocompatible electrically conductive shell to the lid along a second weld line, the second weld line comprising a terminus. The second biocompatible electrically conductive shell can include first and second opposed wide flat sides and first and second opposed narrow flat sides. The narrow flat sides can have a width that is less than that of the wide flat sides. The second biocompatible electrically conductive shell can further include four rounded corners disposed between each wide flat side and an adjacent narrow flat side. The terminus of the second weld line can be disposed on a narrow flat side or a rounded corner.

Other methods and method operations are also included herein as consistent with making and using embodiments of implantable medical devices as described.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. An implantable medical device comprising:
   a power subunit comprising
      a first biocompatible electrically conductive shell defining an open end, a closed end, and an interior volume;
      an anode disposed within the interior volume of the first biocompatible electrically conductive shell;
      a cathode disposed within the interior volume of the first biocompatible electrically conductive shell; and
      a lid occluding the open end of the first biocompatible electrically conductive shell; and
   an electronics control subunit comprising
      a second biocompatible electrically conductive shell;
      a control circuit disposed within the second biocompatible electrically conductive shell;
   wherein the power subunit is coupled to the electronics control subunit and the power subunit is in electrical communication with the electronics control subunit;
   wherein both of the first and second biocompatible electrically conductive shells comprise
      first and second opposed wide sides;
      first and second opposed narrow sides, wherein the narrow sides have a width less than that of the wide sides; and
      four rounded corners disposed at intersections between each wide side and narrow side;
   wherein the first biocompatible electrically conductive shell is welded to the lid around a perimeter of the first biocompatible electrically conductive shell forming a weld line;
   the weld line having a weld line terminus, wherein the weld line terminus is positioned on a narrow side or a rounded corner.

2. The implantable medical device of claim 1, the weld line comprising a laser weld line.

3. The implantable medical device of claim 1, the first biocompatible electrically conductive shell and the second biocompatible electrically conductive shell comprising titanium or a titanium alloy.

4. The implantable medical device of claim 1, wherein the weld line is positioned on a rounded corner.

5. The implantable medical device of claim 1, wherein the weld line exhibits a residual stress that is less than an otherwise identical weld line with the weld line terminus positioned on a wide side.

6. The implantable medical device of claim 1, wherein the second biocompatible electrically conductive shell is welded to the lid around the perimeter of the second biocompatible electrically conductive shell forming a second weld line.

7. The implantable medical device of claim 6, the second weld line having a second weld line terminus, wherein the second weld line terminus is positioned on a narrow side or a rounded corner.

8. The implantable medical device of claim 1, the first and second biocompatible electrically conductive shells having a thickness of 0.006 to 0.012 inches.

9. The implantable medical device of claim 1, the first and second opposed wide sides comprising first and second opposed wide flat sides, and the first and second opposed narrow sides comprising first and second opposed narrow flat sides.

10. A method of making an implantable medical device comprising
   obtaining a biocompatible electrically conductive shell, the biocompatible electrically conductive shell defining an interior volume, an open end and a closed end;
   positioning a lid to occlude the open end of the biocompatible electrically conductive shell; and
   welding the biocompatible electrically conductive shell to the lid along a weld line, the weld line comprising a terminus;
   wherein the biocompatible electrically conductive shell comprises first and second opposed wide flat sides, first and second opposed narrow flat sides, wherein the narrow flat sides have a width less than that of the wide flat sides; and four rounded corners disposed between each wide flat side and an adjacent narrow flat side;
   wherein the terminus of the weld line is disposed on a narrow flat side or a rounded corner.

11. The method of claim 10, further comprising welding a second biocompatible electrically conductive shell to the lid along a second weld line, the second weld line comprising a terminus
   the second biocompatible electrically conductive shell comprising first and second opposed wide flat sides, first and second opposed narrow flat sides, wherein the narrow flat sides have a width less than that of the wide flat sides; and four rounded corners disposed between each wide flat side and an adjacent narrow flat side;
   wherein the terminus of the second weld line is disposed on a narrow flat side or a rounded corner.

12. An implantable medical device comprising:
   a power subunit comprising
      a first biocompatible electrically conductive shell;
      an anode disposed within the first biocompatible electrically conductive shell; and
      a cathode disposed within the first biocompatible electrically conductive shell; and
      a lid;
   wherein the lid comprises a central body, a first extended rim surrounding the central body, and a second extended rim surrounding the central body, wherein the second extended rim faces in a direction opposite that of the first extended rim; and
   wherein the first biocompatible electrically conductive shell is welded to the first extended rim of the lid.

13. The implantable medical device of claim 12, wherein the first extended rim is separated from the central body by a relief channel.

14. The implantable medical device of claim 12, wherein the first extended rim and the first biocompatible electrically conductive shell form a butt joint.

15. The implantable medical device of claim 12, wherein the first extended rim and the first biocompatible electrically conductive shell form an overlap joint.

16. The implantable medical device of claim 12, wherein the first extended rim overlaps the first biocompatible electrically conductive shell.

17. The implantable medical device of claim 12, wherein the first biocompatible electrically conductive shell comprises, in cross-section, first and second opposed wide flat sides, first and second opposed narrow flat sides, wherein the narrow flat sides have a width less than that of the wide flat sides; and four rounded corners disposed between each wide flat side and an adjacent narrow flat side;
   wherein the first biocompatible electrically conductive shell is welded to the lid around a perimeter thereof forming a weld line;

the weld line having a weld line terminus, wherein the weld line terminus is positioned on a narrow flat side or a rounded corner.

18. The implantable medical device of claim 17, the weld line comprising a laser weld line.

19. The implantable medical device of claim 12, the first biocompatible electrically conductive shell comprising titanium or a titanium alloy.

\* \* \* \* \*